United States Patent [19]

Pelosi, Jr.

[11] 4,161,479
[45] Jul. 17, 1979

[54] 5-(4-CHLOROPHENYL)FURFURYLUREA

[75] Inventor: Stanford S. Pelosi, Jr., Norwich, N.Y.

[73] Assignee: Morton-Norwich Products, Inc., Norwich, N.Y.

[21] Appl. No.: 922,860

[22] Filed: Jul. 10, 1978

[51] Int. Cl.$^2$ ............................................. C07D 307/54
[52] U.S. Cl. ................................. 260/347.3; 424/285
[58] Field of Search ....................................... 260/347.3

[56] References Cited

U.S. PATENT DOCUMENTS 3,098,791   7/1963   Fander ......................... 260/553 R X Primary Examiner—Richard Raymond
Attorney, Agent, or Firm—Anthony J. Franze

[57] ABSTRACT

5-(4-Chlorophenyl)furfurylurea us useful as an anti-inflammatory agent.

1 Claim, No Drawings

5-(4-CHLOROPHENYL)FURFURYLUREA

This invention relates to the compound 5-(4-chlorophenyl)furfurylurea of the formula:

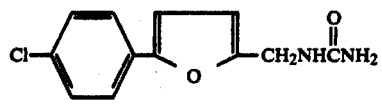

and a method for its preparation.

This compound possesses pharmacologic activity. It is particularly useful as an anti-inflammatory agent as evidenced by its ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited by 92% [Winter et al., P.S.E.B.M. 111:544(1962)].

The compound of this invention is readily prepared. Currently, it is preferred to react 5-(4-chlorophenyl)furfurylamine with an aqueous solution of potassium cyanate in the presence of a solvent such as glacial acetic acid.

In order that this invention may be fully available to and understood by those skilled in the art, the method now preferred for making it is described:

5-(4-Chlorophenyl)furfurylamine hydrochloride (122 g, 0.50 mole) was added to a stirred solution of 10% sodium carbonate. The mixture was extracted with hot ethyl acetate several times. The solvent was removed on a rotary evaporator to leave a residual oil which solidified on cooling. This free base (104 g) was dissolved in 800 ml of glacial acetic acid with heating and cooling to 27°. A solution of 81 g (1.0 mole) of potassium cyanate in 600 ml of water was added over 5 min. and stirring was continued overnight at ambient temperature. The solid was collected by filtration, washed with water and dried in 60° oven to give 64 g. The filtrate was diluted to 4.1 with water and ice. The solid was collected by filtration, washed with water and dried in 60° oven to give 8 g. Total yield of 5-(4-chlorophenyl)furfurylurea was 72 g (58%). Four recrystallizations from $CH_3CN$ gave an analytical sample, m.p. 210–211°.

Anal. Calcd. for $C_{12}H_{11}ClN_2O_2$: C, 57.49%; H, 4.42%; N, 11.18%. Found: C, 57.39%; H, 4.55%; N, 11.24%.

What is claimed is:
1. The compound 5-(4-chlorophenyl)furfurylurea.